United States Patent [19]

Ferris

[11] Patent Number: 4,689,401
[45] Date of Patent: Aug. 25, 1987

[54] METHOD OF RECOVERING MICROBIALLY PRODUCED RECOMBINANT RICIN TOXIN A CHAIN

[75] Inventor: Robert Ferris, Walnut Creek, Calif.

[73] Assignee: Cetus Corporation, Emeryville, Calif.

[21] Appl. No.: 905,283

[22] Filed: Sep. 9, 1986

Related U.S. Application Data

[63] Continuation-in-part of Ser. No. 836,848, Mar. 6, 1986, abandoned.

[51] Int. Cl.$^4$ .......................... C07K 1/14; C07K 3/22; C07K 3/28; C07K 13/00
[52] U.S. Cl. ..................................... 530/396; 424/85; 424/88; 435/68; 435/70; 435/172.2; 435/172.3; 530/377; 530/403; 530/808; 530/809; 530/416
[58] Field of Search ............... 530/377, 396, 397, 403, 530/416, 808, 809; 424/85, 88; 435/68, 70, 172.3, 240, 241, 172.3

[56] References Cited

U.S. PATENT DOCUMENTS

| | | | |
|---|---|---|---|
| 4,340,535 | 7/1982 | Voisin et al. | 424/85 X |
| 4,414,148 | 11/1983 | Jansen et al. | 424/85 X |
| 4,590,071 | 5/1986 | Scannon et al. | 424/85 |
| 4,614,650 | 9/1986 | Jansen et al. | 424/85 |

OTHER PUBLICATIONS

Proc-Natl. Acad. Sci., USA 77, No. 9 (1980), 5419–5422, Krolick et al.
Monoclonal Antibodies in Clinical Medicine, Academic Press Thorpe et al., 168–190 (1982).
Eur. J. Biochem., 116(1981), 447–454, Thorpe et al.
Toxicon, (1984), 22(2), 265–277, Cushley et al.
Analytical Biochemistry, 146, 206–210 (1985), Simmons et al.
Clinical Allergy, (1983), 13, 553–561, Davison et al.
Perspectives in Toxicology, Bernheimer Ed. 1977, pp. 122–147, Olsnes.
Europ. J. Biochem. 137, 57–65 (1983), Butterworth et al.
Molecular Action of Toxins & Viruses, Elsevier Biomedical Press, 1982, pp. 51–105, Olsnes et al.

Primary Examiner—Howard E. Schain
Attorney, Agent, or Firm—Thomas E. Ciotti; Elliott L. Fineman

[57] ABSTRACT

Substantially pure, intracellularly produced, soluble recombinant ricin toxin A (RTA) is recovered from transformed cells by disrupting the cell membrane, removing insoluble cell membrane materials from the disruptate, adjusting the pH of the cell membrane material-free solution to 6 to 6.5 and the conductivity to 1.25 to 1.75 millisiemens, passing the adjusted solution through a bed of SP-cellulose cation exchanger, and eluting the substantially pure RTA from the bed.

22 Claims, 2 Drawing Figures (HindIII)
(1) ccaagaattgctgcaaaagcttatgaaaccggg
TCTTCCTCAGCTGCTCACTTTCCAATAAAATTCCAAGAATTGCTGCAATCAAAGATGAAACCGGGAGGAAATACT
                                                        METLysProGlyGlyAsnThr BamH1            (2) ctttcacattagag
ATTGTAATATGGATGTATGCAGTGGCAACATGGCTTTGTTTTGGATCCACCTCAGGGTGGTCTTTCACATTAGAG
IleValIleTrpMETTyrAlaValAlaThrTrpLeuCysPheGlySerThrSerGlyTrpSerPheThrLeuGlu
(HindIIIMET)                                        --- <------(leader) <-----
aagcttatgatattccccaaac
GATAACAACATATTCCCCAAACAATACCCAATTATAAACTTTACCACAGCGGGTGCCACTGTGCAAAGCTACACA
AspAsnAsnIlePheProLysGlnTyrProIleIleAsnPheThrThrAlaGlyAlaThrValGlnSerTyrThr
RTA- <--------IlePheProLysGlnTyrProIleIleAsnPheThrThrAlaGlyAlaThrValGlnSerTyrThr

AACTTTATCAGAGCTGTTCGCGGTCGTTTAACAACTGGAGCTGATGTGAGACATGAAATACCAGTGTTGCCAAAC
AsnPheIleArgAlaValArgGlyArgLeuThrThrGlyAlaAspValArgHisGluIleProValLeuProAsn
RTA-AsnPheIleArgAlaValArgGlyArgLeuThrThrGlyAlaAspValArgHisGluIleProValLeuProAsn

AGAGTTGGTTTGCCTATAAACCAACGGTTTATTTTAGTTGAACTCTCAAATCATGCAGAGCTTTCTGTTACATTA
ArgValGlyLeuProIleAsnGlnArgPheIleLeuValGluLeuSerAsnHisAlaGluLeuSerValThrLeu
RTA-ArgValGlyLeuProIleAsnGlnArgPheIleLeuValGluLeuGlnAsnHisAlaGluIleSerValThrLeu

GCGCTGGATGTCACCAATGCATATGTGGTAGGCTACCGTGCTGGAAATAGCGCATATTTCTTTCATCCTGACAAT
AlaLeuAspValThrAsnAlaTyrValValGlyTyrArgAlaGlyAsnSerAlaTyrPhePheHisProAspAsn
RTA-AlaLeuSerValThrAsnAlaTyrValValGlyTyrArgAlaGlyAsnSerAlaTyrPhePheHisProAspAsn

CAGGAAGATGCAGAAGCAATCACTCATCTTTTCACTGATGTTCAAAATCGATATACATTCGCCTTTGGTGGTAAT
GlnGluAspAlaGluAlaIleThrHisLeuPheThrAspValGlnAsnArgTyrThrPheAlaPheGlyGlyAsn
RTA-GlnGluAspAlaGluAlaIleThrHisLeuPheThrAspValGlnAsnArgTyrThrPheAlaPheGlyGlyAsn

TATGATAGACTTGAACAACTTGCTGGTAATCTGAGAGAAAATATCGAGTTGGGAAATGGTCCACTAGAGGAGGCT
TyrAspArgLeuGluGlnLeuAlaGlyAsnLeuArgGluAsnIleGluLeuGlyAsnGlyProLeuGluGluAla
RTA-TyrAspArgLeuGluGlnLeuAlaGlyAsnLeuArgGluAsnIleGluLeuGlyAsnGlyProLeuGluGluAla

ATCTCAGCGCTTTATTATTACAGTACTGGTGGCACTCAGCTTCCAACTCTGGCTCGTTCCTTTATAATTTGCATC
IleSerAlaLeuTyrTyrTyrSerThrGlyGlyThrGlnLeuProThrLeuAlaArgSerPheIleIleCysIle
RTA-IleSerAlaLeuTyrTyrTyrSerThrGlyGlyThrGlnLeuProThrLeuAlaArgSerPheIleIleCysIle

CAAATGATTTCAGAAGCAGCAAGATTCCAATATATTGAGGGAGAAATGCGCACGAGAATTAGGTACAACCGGAGA
GlnMETIleSerGluAlaAlaArgPheGlnTyrIleGluGlyGluMETArgThrArgIleArgTyrAsnArgArg
RTA-GlnMetIleSerGluAlaAlaArgPheGlnTyrIleGluGlyGluMetArgThrArgIleArgTyrAsnArgArg

TCTGCACCAGATCCTAGCGTAATTACACTTGAGAATAGTTGGGGGAGACTTTCCACTGCAATTCAAGAGTCTAAC
SerAlaProAspProSerValIleThrLeuGluAsnSerTrpGlyArgLeuSerThrAlaIleGlnGluSerAsn
RTA-SerAlaProAspProSerValIleThrLeuGluAsnSerTrpGlyArgLeuSerThrAlaIleGlnGluSerAsn

CAAGGAGCCTTTGCTAGTCCAATTCAACTGCAAAGACGTAATGGTTCCAAATTCAGTGTGTACGATGTGAGTATA
GlnGlyAlaPheAlaSerProIleGlnLeuGlnArgArgAsnGlySerLysPheSerValTyrAspValSerIle
RTA-GlnGlyAlaPheAlaSerProIleGlnLeuGlnArg AspGlySerLysPheSerValTyrAspValSerIle
(TER)
(3) cacagttttaattgcttataagg
TTAATCCCTATCATAGCTCTCATGGTGTATAGATGCGCACCTCCACCATCGTCACAGTTTTCTTTGCTTATAAGG
LeuIleProIleIleAlaLeuMETValTyrArgCysAlaProProProSerSerGlnPheSerLeuLeuIleArg
RTA-LeuLeuProIleIleAla MetValTyrArgCysAlaProProProSerSerGlnPhe(<--A-chain)

BamH1
CCAGTGGTACCAAATTTTAATGCTGATGTTTGTATGGATCCTGAGCCCATAGTGCGTATCGTAGGTCGAAATGGT
ProValValProAsnPheAsnAlaAspValCysMETAspProGluProIleValArgIleValGlyArgAsnGly
RTB- (B-chain-> )AlaAspValCysMetAspProGluProIleValArgIleValGlyArgAsnGly

FIG. 1 ed. Such modifications are included within the definition so long as the cytotoxic activity is retained.

"Recombinant" RTA refers to RTA that has been produced by genetically engineered microorganisms. "Substantially pure" RTA refers to RTA which is at least 90% by weight RTA, as determined by SDS-PAGE.

METHOD OF RECOVERING MICROBIALLY PRODUCED RECOMBINANT RICIN TOXIN A CHAIN

DESCRIPTION

This is a continuation-in-part application of U.S. patent application Ser. No. 06/836,848 filed Mar. 6, 1986, now abandoned.

TECHNICAL FIELD

This invention is in the field of biochemical engineering. More particularly, the invention concerns a biochemical separation or recovery process in which recombinant ricin toxin A chain (RTA) is recovered from microorganisms that have been genetically engineered to produce RTA.

BACKGROUND ART

Ricin toxin is a naturally occurring toxin that is derived from the seeds of *Ricinus communis*, commonly known as castor beans. It is composed of an enzymatically active cytotoxic polypeptide chain, commonly called the "A" chain and sometimes referred to herein as "RTA", that is bound by a single disulfide link to a second polypeptide chain commonly called the "B" chain that is presumed to be responsible for binding the toxin molecule to cells and aiding in translocating RTA into the cytoplasm. RTA is capable of catalytically inactivating the large subunit of ribosomes in vitro and the mechanism of RTA for in vivo cytotoxicity is believed to reside in this capacity for ribosome inactivation.

Olsnes, S. *Perspectives in Toxicology*, A. W. Bernheimer, Ed (1977) J. Wiley & Sons, NY, pp 122-147 and Olsnes, S., et al., *Molecular Action of Toxins and Viruses*, Cohen, et al, Ed (1982) Elsevier, Amsterdam, pp 51-105 characterize native RTA as having an apparent molecular weight of 32,000. Copending commonly owned U.S. patent application Ser. No. 715,934 filed Mar. 25, 1985 discloses the native structural gene for RTA, the deduced amino acid sequence of RTA, DNA constructs for cloning and expressing the RTA gene, and transformed bacteria capable of synthesizing intracellularly produced, soluble recombinant RTA. The patent application further describes the production of such recombinant RTA by such bacteria and a procedure for recovering RTA from the bacteria. The recovery procedure comprises sonicating the cells in an aqueous suspension under reducing conditions at a pH of 8.5, centrifuging the sonicate, and chromatographing the supernatant using a phenylsepharose column to produce a partially purified soluble form of RTA. This RTA was further purified by successive chromatographing on a carboxymethyl cellulose column and a Cibacron Blue F3GA column. While this recovery process provides substantially pure RTA, it is tedious and suffers from low yields.

The present invention provides a simpler procedure for recovering substantially pure, soluble recombinant RTA in higher yields from the transformants.

DISCLOSURE OF THE INVENTION

The novel method of this invention for recovering intracellularly produced recombinant ricin toxin A, chain (RTA) from an aqueous suspension of transformed microorganisms containing the RTA comprises:

(a) disrupting the cell membrane of the microorganisms at a pH above about 7;

(b) removing insoluble cell membrane materials from the disruptate at a pH above about 7;

(c) adjusting the pH of the solution resulting from step (b) to about 6 to about 6.5 and the conductivity of said solution to about 1.25 to about 1.75 millisiemens;

(d) then passing said solution through a bed of an SP-cellulose cation exchanger, whereby RTA in the solution is retained by the exchanger; and (e) eluting RTA from the bed to produce a solution whose protein content is at least about 90% by weight RTA as determined by SDS-PAGE.

Preferably, the steps of the method are carried out singly or in combination at a temperature at which the formation of precipitates including RTA is reduced.

The invention further comprises RTA produced by the method as well as purified RTA.

BRIEF DESCRIPTION OF THE DRAWING

FIG. 1 shows the complete nucleotide sequence of the cloned insert of pRA123 which encodes RTA and the deduced amino acid sequence of RTA.

MODES OF CARRYING OUT THE INVENTION

A. Definitions

Figure 2:
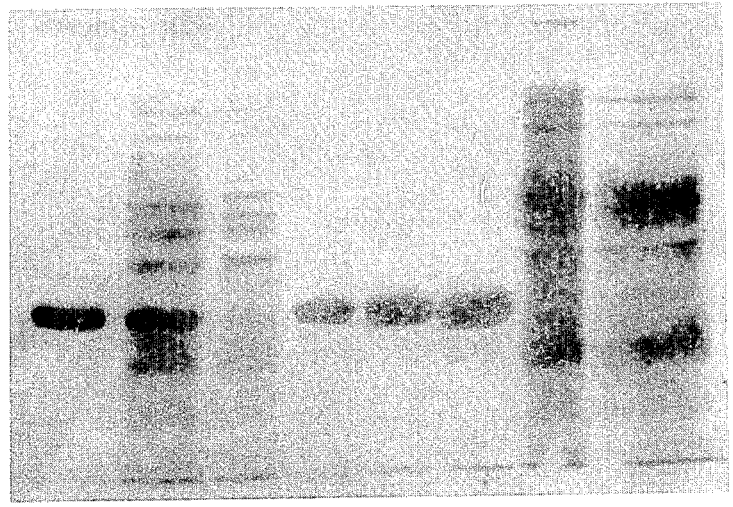
FIG. 2 shows SDS-PAGE analysis of the RTA produced by the method of the invention and the reduced formation of precipitates that include RTA.

As used herein, "ricin toxin A" or "RTA" refers to a protein whose amino acid sequence is substantially similar to that of the ricin A peptide which is extractable from castor bean seeds. The RTA of castor beans is approximately 265 amino acids in length and has a molecular weight of approximately 32,000 daltons. However, it is known that the precise sequence varies depending on the variety of bean, and, indeed, that at least two slightly different forms of RTA may be present in a single variety of bean.

In connection with describing equivalents of native RTA, the term "substantially similar" means that the polypeptide in question must be approximately the same length (arbitrarily within around 10%, although it is known that the essential features for activity may reside in a peptide of shorter length—i.e., a "fragment", or of longer sequence—i.e., a fusion protein), but more importantly, and critical to the definition, must retain the capacity of the A chain to interact with, and incapacitate, the 60S ribosome subunit. Alterations in chain length which do not greatly impair this enzymatic activity are included. It is well known that some small alterations in protein sequence may be possible without disturbing the functional abilities of the protein molecule, although other modifications are totally destructive. It is not currently possible to predict with any assurance into which category a particular alteration will fall. The definition herein permits any modifications which are in the first category. Such alterations could result from chance mutations in the gene sequence or from deliberate alteration thereof. In summary, modified forms of amino acid sequence which retain the cytotoxic activity of RTA are included.

Further, as is well known, protein sequence may be modified by post-translational processing such as association with other molecules, for example, glycosides, lipids, or such inorganic ions as phosphate. The ionization status will also vary depending on the pH of the medium or the pH at which crystallization or precipitation of the isolated form occurs. Further, the presence of air may cause oxidation of labile groups, such as —SH. Included within the definition of RTA are all such modifications of a particular primary structure— e.g., both glycosylated and nonglycosylated forms, neutral forms, acidic and basic salts, lipid or other associated peptide forms, side chain alterations due to oxidation or derivatization, and any other such modifications of an amino acid sequence which would be encoded by the same genetic codon sequence.

As used herein, "soluble" refers to recombinant RTA which remains in the supernatant after centrifugation for 30 min at 100,000×g in aqueous buffer under physiologically isotonic conditions, for example, 0.14M sodium chloride or sucrose, at a protein concentration of as much as 10 mg/ml. These conditions specifically relate to the absence of detergents or other denaturants in effective concentrations such as guanidine or urea.

"Transformed microorganism" means an organism that has been genetically engineered to produce soluble RTA. Examples of such organisms are described in said U.S. patent application Ser. No. 715,934 and the examples of this application. Bacteria are preferred microorganisms for producing recombinant RTA for recovery in accordance with this invention, although recombinant RTA may also be made by suitably transformed eukaryotic hosts, such as yeast cells. *E. coli* is a particularly preferred host.

B. Microbial Production of RTA

DNA constructs and transformed microorganisms used to synthesize soluble, intracellularly produced recombinant RTA are described in said copending U.S. application Ser. No. 715,934, the disclosure of which is incorporated by reference.

FIG. 1 shows a cloned cDNA insert of pRA123 (deposited with the ATCC on Aug. 14, 1984 under accession No. 39799), which encodes RTA and that was used to produce such RTA. This insert was modified by primer directed mutagenesis to place a HindIII site in front of a newly constructed ATG start codon preceding the RTA structural gene and to place a stop codon at the C-terminus to provide a properly terminating coding sequence for RTA that could be removed as a HindIII/BamHI cassette and ligated into an appropriate expression vector. Preferred expression control sequences employ the alkaline phosphatase A (pho A) promoter/operator and leader sequence and the positive retroregulator derived from *B. thuringiensis* crystal protein gene. The expression control sequences and the coding sequence were combined to form the expression vector pRAP229 (deposited at the ATCC on Mar. 8, 1985 under accession No. 53408). In this expression system, the essential component is the terminated phoA leader sequence upstream of, proximal to, and out of phase with the RTA encoding sequence, wherein the RTA encoding sequence is initiated by an ATG start codon.

This expression system is transformed into a suitable bacterial host such as *E. coli* MM294. Transformed cultures are grown in a suitable growth medium under conventional conditions such as those described in Michaelis et al, *J. Bact* (1983) 154:356–365. Expression of RTA by the cells may be delayed by maintaining the cells in the presence of phosphate until the desired level of growth is achieved and then lowering the phosphate levels when expression is desired. After inducing the cells, the cells are harvested and concentrated, if necessary, to provide an aqueous suspension of cells by filtration, centrifugation, or other known procedures.

C. Recovery of RTA from Cells

The cell membranes of the transformants are disrupted under reducing conditions to release the intracellularly produced soluble RTA into the suspending medium. The pH of the medium is maintained at a level that keeps the RTA in solution (above about 7, preferably at 8.5 to 8.8) in the disruption step. Disruption may be effected by high pressure cycling and monitored by optical density. Reducing conditions are maintained by adding an effective amount of a reducing agent such as dithiothreitol or 2-mercaptoethanol to the medium.

Following disruption, insoluble cell membrane materials are removed from the disruptate by centrifugation or, preferably, diafiltration. pH is kept alkaline as above to keep the RTA in solution.

After removal of the insoluble cellular materials, the pH and conductivity of the resulting solution are adjusted for the following preparative ion exchange chromatography step. The pH is buffered to between about 6 and 6.5, preferably using phosphate, and the conductivity is adjusted to between about 1.25 and 1.75 millisiemens, preferably about 1.45 to 1.55 millisiemens. Conductivity may be increased by adding suitable ionic species or lowered by dilution. The conductivity of the solution affects the efficiency of the subsequent SP-cellulose chromatography step in terms of (1) the binding capacity of the exchanger, (2) maintaining the RTA in solution, and (3) binding of contamination proteins. Significantly higher conductivities than those indicated above affect the binding capacity of the exchanger adversely, whereas significantly lower conductivities tend to cause the RTA to precipitate and increase the binding of contaminating proteins.

The solution is then passed through one or more beds of equilibrated SP-cellulose cation exchanger to separate the RTA from the solution. The SP-cellulose cation exchanger is an elastic three-dimensional network composed of cellulosic backbones cross-linked with vinyl polymer carrying pendant sulfopropyl functional group. The bed is preferably adapted for radial flow passage of the solution. Such beds are available commercially from AMF Molecular Separations Division, Meridian, CT, under the brand name ZetaPrep SP Cartridges. Flow rates of the solution will depend upon the size and geometry of the bed. Care should be taken to avoid exceeding the capacity of the bed. If the capacity is exceeded, the RTA will not be retained and will be present in the effluent from the bed. Bed capacity may, accordingly be monitored by tracking the levels of RTA in the effluent. A series of beds may be used to avoid loss of RTA in the effluent. Alternatively, when maximum bed capacity is reached, the bed may be eluted and regenerated. The bed may be equilibrated before use with phosphate buffer, pH 6.5, 0.1% β-mercaptoethanol (or other suitable reducing agent).

RTA may be eluted from the bed using solutions which alter the pH or conductivity such that the RTA dissociates from the bed. Gradient or nongradient elution may be used. A preferred elutant is 1M NaCl.

In a preferred embodiment, all steps from the disruption of the RTA-producing cells through elution from the SP-cellulose cation exchanger are carried out at a temperature sufficiently cold to reduce or eliminate the formation of precipitates of RTA either with itself or with components of the cell or cell components, including proteins extracted from the cell. In general, this temperature is in a range below 10° C. but high enough that the solutions used to suspend, extract, and elute the cells and RTA do not freeze. More preferred is a temperature of 2°–8° C. Most preferred is a temperature of about 4° C.

The protein content of the resulting eluate is at least about 90% and more usually at least 95% by weight RTA. The pyrogen content of this substantially pure RTA is less than about 100 ng/mg RTA. Yields typically range between 80% and 90%. In this regard, prior procedures that used to recover soluble RTA of such purity from transformed microorganisms involved multiple chromatographic steps (none of which involved SP-cellulose exchangers) and had much lower yields.

The RTA may be further purified to levels in excess of 99% by subjecting the eluate from the SP-cellulose exchanger to preparative chromatography using an equilibrated phenyl-sepharose column. The RTA may be eluted from the column using a propylene glycol or glycerol gradient.

D. Examples

The following examples further illustrate the RTA recovery process of the invention. The examples are not intended to limit the invention in any manner.

EXAMPLE 1

Production of Cells

*E. coli* MM294 transformed with pRAP229 were grown under conditions similar to those described by Michaelis et al, supra. The transformants were induced by lowering the exogenous phosphate concentration and maintaining the culture for 16-17 hr. Following induction, the cultures was frozen at −20° C.

Disruption

A 336 g portion of frozen cells was thawed and resuspended in 3 L of 0.1 M glycine, pH 8.8, 1 mM ethylenediaminetetraacetic acid (EDTA) and 0.1% 2-mercaptoethanol. The suspension was passed three times through a Manton-Gaulin homogenizer (6000-7000 psi). The disruptate was a syrupy suspension after three passes.

Diafiltration

Three liters of disruptate were diafiltered in an Amicon DC10L unit using a 10 sq. ft. Microgen cellulose cartridge. The resuspending medium described above was used as a diafiltration buffer. The inlet pressure was 20 psi and the outlet pressure was 15 psi. The disruptate volumn was reduced to approximately 1.5 L. Approximately 17.5 L of diafiltrate, pH 8.8, conductivity 0.96 millisiemens, was collected in four fractions. Protein analysis of the diafiltrate indicated that it contained approximately 19.9 g protein. The diafiltrate was titrated to pH 6.5 with 1 M phosphoric acid to avoid localized precipitation. The conductivity of the solution after titration was 1.0 millisiemens and its volume was 19.5 L. The conductivity was raised to 1.31 millisiemens by the addition of approximately 30 ml of 1 M $NaH_2PO_4$.

SP-Cellulose Ion Exchange Chromatography

A 250 cc ZetaPrep SP cartridge and a 1000 cc ZetaPrep SP cartridge were connected in series. The inlet to the 250 cc cartridge was coupled to a vessel holding the adjusted diafiltrate via a pump and the outlet from the 1000 cc cartridge was connected via an $A_{280}$ detector to a fraction collector.

The cartridges were activated by consecutive washes with (1) 5 L of 0.1 M $Na_3PO_4$, (2) 0.7 L of 0.1 M acetic acid, (3) 2 L of 0.2 M phosphate, pH 6.5, (4) 5.6 L of 10 mM phosphate, pH 6.5, 0.1% 2-mercaptoethanol.

The adjusted diafiltrate was pumped through the cartridges at 80 ml/min (20 psi back pressure) and the effluent was collected in 2 L fractions. Every fraction was assayed by SDS-PAGE. The SDS-PAGE analyses showed little or no RTA in the effluent fractions.

After the 19.5 L of diafiltrate had been passed through the cartridges, the cartridges were washed with 10 mM phosphate, pH 6.5, 0.1% 2-mercaptoethanol until the $A_{280}$ reached baseline. The cartridges were uncoupled and bound RTA was eluted separately in 2000 ml fractions from them with elution buffer (20 mM phosphate, pH 6.5, 0.1% 2-mercaptoethanol, 1M sodium chloride). Fraction 14 from the 250 cc cartridge was found to contain >95% of the RTA in the diafiltrate. This indicates that the capacity of this 250 cc (at 1.31 millisiemens) was sufficient to isolate the RTA from a 19.5 L volume of diafiltrate. Approximately 2.74 g of substantially pure (>95% measured by SDS-PAGE) RTA was recovered from fraction 14.

EXAMPLE 2

This example shows the effect of varying the conductivity of the RTA solution that is applied to the SP-cellulose exchanger.

Equilibration of Exchanger

ZetaPrep SP15 cartridges were washed sequentially with 100-200 ml of 0.1M sodium phosphate and 30-50 ml of 0.1M acetic acid at 5 ml/min. The cartridge was then equilibrated with 10-20 mM phosphate, pH 6.5, 0.1% 2-mercaptoethanol.

Samples of unadjusted diafiltrate (Example 1) were adjusted to pH 6.5 and to conductivities of 1.0, 1.26, and approximately 2.2 millisiemens and were charged to the cartridges at 3-5 ml/min. The effluent was collected in ~450 ml fractions.

After an entire sample had been passed through a cartridge, the cartridge was washed with equilibration buffer until the $A_{280}$ reached baseline. The retained RTA was then eluted with elution buffer (20 mM phosphate, pH. 6.5, 0.1% 2-mercaptoethanol, 1.0 M NaCl). The RTA contents of the retentates were determined by $A_{280}$ absorbance measurements and SDS-PAGE analyses. The extent of RTA precipitation was evaluated visually.

The table below reports the binding capacity (in mg) for each run and the observed degree of precipitation.

| | Sample | | |
|---|---|---|---|
| | 1.0 | 1.26 | 2.2 |
| RTA binding capacity | 200 | 181 | 115 |
| Precipitation | high | low | negligible |

As indicated, the best balance of capacity and solubility occurred at a conductivity of 1.26 millisiemens in these tests.

EXAMPLE 3

This example illustrates the use of an alternate SP-cellulose exchanger.

A 1×10 cm column (7.85 ml) of Trisacryl MSP resin was prepared and equilibrated with equilibration buffer. A 50 ml sample of the 1.0 millisiemen adjusted diafiltrate of Example 2 was loaded into the column at a flow rate of 25 ml/hr. The column was then washed with equilibration buffer until the $A_{280}$ had returned to baseline and eluted with elution buffer. SDS-PAGE analyses were run on diafiltrate effluent from the column and the column retentate. These analyses showed that a significant amount of RTA bound to the column but that a significant amount was also present in the diafiltrate effluent. Accordingly, the Trisacryl MSP resin did not appear to be a effective as the ZetaPrep SP cartridge in chromatographing RTA.

EXAMPLE 4

10 gm of *E. Coli* MM294 transformed with pRAP 229 were obtained after growth and induction as described in Example 1, and were suspended in 100 ml 0.1M glycine, 1 mM EDTA, 0.1% 2-mercaptoethanol (BME), pH 8.8. The cell suspension was sonicated in an M-195 Heat Systems Ultrasonics cell disrupter W-375, 50% duty cycle at 8.0 output for 1 minute. The disruptate was centrifuged at 4° C., at 10,000 rpm in a SS34 rotor Sorvall RC5 centrifuge ~(12,000×g) for 30 minutes. The supernatant was decanted and stored at 40° C. The pellet was resuspended in buffer, sonicated and centrifuged as above. The supernatants were combined and yielded a volume of 196 ml which was stored at 4° C. In all of the following steps the sRTA supernatant solutions and columns were maintained at 4° C.

The supernatant was filtered through a 0.2 μM Nalgene filter and the retentate was discarded. The supernatant was titrated to pH 6.5 with 1M $H_3PO_4$, and the conductivity was adjusted to 1.5 mS with 0.1M $Na_3PO_4$ and the pH readjusted to 6.5 with $H_3PO_4$. No precipitate was observed during the pH or conductivity titrations.

A Zeta Prep SP disc (AMF separation SP00107) was activated with 300 ml 0.1M $Na_3PO_4$ and 300 ml acetic acid and was equilibrated with 600 ml 10 mM $NaPO_4$, 1 mM EDTA, 0.1% BME, pH 6.5.

The adjusted sample was loaded on the zeta prep disc at a flow rate of 5 ml/min. The loaded zeta prep disc was washed with 10 mM $Na_3PO_4$, 1 mM EDTA, 0.1% BME pH 6.5 until absorbance at 280 mM equalled 0 and sample was eluted with 213 ml of 100 mM $NaPO_4$, 1 mM EDTA, 1 M NaCl, 0.1% BME, pH 6.5.

2.5 ml of the retentate was desalted by size exclusion chromatography (G-25 Sephadex) PD 10 column (Pharmacia Uppsula, Sweden) in PBS. 3.5 ml of desalted retentate was collected. A single peak was observed at 280 nM.

The solution loaded onto the Zeta Prep (lane 2) disc; flow through (lane 3), desalted retentate (lanes 4, 5, 6), loading supernatant (lane 7), and load precipitate (lane 8), (the latter two fractions, obtained as in Example 1) were subjected to 12% SDS-PAGE. An sRTA standard (lane 1) was also run. The results of these SDS-PAGE analyses are shown in FIG. 2.

Modifications of the above-described modes for carrying out the invention that are obvious to those of skill in the fields of genetic engineering, biochemistry, and chemical engineering are intended to be within the scope of the following claims.

I claim:

1. Method of recovering recombinant intracellularly produced, soluble ricin toxin A chain (RTA) from an aqueous suspension of transformed microorganisms containing the RTA comprising:

(a) disrupting the cell membrane of the microorganisms at a pH that keeps the RTA in solution;

(b) removing insoluble cell membrane materials from the disruptate at a pH that keeps the RTA in solution;

(c) adjusting, if necessary, the pH of the solution resulting from step (b) to about 6 to about 6.5 and the conductivity of said solution to about 1.25 to about 1.75 millisiemens;

(d) then passing said solution through a bed of an SP-cellulose cation exchanger, whereby RTA in the solution is retained by the exchanger; and (e) eluting RTA from the bed to produce a solution whose protein content is at least about 90% by weight RTA as determined by SDS-PAGE.

2. The method of claim 1 wherein step (a) is effected by high pressure cycling and is carried out under reducing conditions.

3. The method of claim 1 wherein step (b) is effected by diafiltration.

4. The method of claim 1 wherein said conductivity is about 1.45 to about 1.55.

5. The method of claim 1 wherein the cation exchanger is composed of cellulosic backbones crosslinked with vinyl polymer carrying pendant sulfopropyl functional groups and the bed is configured such that the solution is passed radially through the bed.

6. The method of claim 1 wherein said protein content is at least about 95% by weight RTA as determined by SDS-PAGE.

7. The method of claim 5 wherein step (a) is effected by high pressure cycling, step (b) is effected by diafiltration, the conductivity is about 1.45 to about 1.55 millisiemens, and the protein content is at least about 95% by weight RTA as determined by SDS-PAGE.

8. The method of claim 1 including (f) chromatographing the eluted RTA using a phenyl-sepharose column, whereby the purity of the RTA is increased to above about 99%.

9. The method of claim 1 wherein steps a-f are singly or in combination run at a temperature that reduces formation of precipitates comprising RTA.

10. The method of claim 9 wherein said temperature is in a range from one sufficient to keep solutions from freezing to about 10° C.

11. The method of claim 9 wherein said temperature is about 4° C.

12. Ricin toxin A chain (RTA) recovered from an aqueous suspension of transformed microorganisms containing the RTA by the steps comprising:

(a) disrupting the cell membrane of the microorganisms at a pH that keeps the RTA in solution;

(b) removing insoluble cell membrane materials from the disruptate at a pH that keeps the RTA in solution;

(c) adjusting, if necessary, the pH of the solution resulting from step (b) to about 6 to about 6.5 and the conductivity of said solution to about 1.25 to about 1.75 millisiemens;

(d) then passing said solution through a bed of an SP-cellulose cation exchanger, whereby RTA in the solution is retained by the exchanger; and (e) eluting RTA from the bed to produce a solution whose protein content is at least about 90% by weight RTA as determined by SDS-PAGE.

13. Ricin toxin A chain of claim 12 wherein step (a) is effected by high pressure cycling and is carried out under reducing conditions.

14. Ricin toxin A chain of claim 13 wherein step (b) is effected by diafiltration.

15. Ricin toxin A chain of claim 12 wherein said conductivity is about 1.45 to about 1.55.

16. Ricin toxin A chain of claim 12 wherein the cation exchanger is composed of cellulosic backbones cross-linked with vinyl polymer carrying pendant sulfopropyl functional groups and the bed is configured such that the solution is passed radially through the bed.

17. Ricin toxin A chain of claim 12 wherein said protein content is at least about 95% by weight RTA as determined by SDS-PAGE.

18. Ricin toxin A chain of claim 16 wherein step (a) is effected by high pressure cycling, step (b) is effected by diafiltration, the conductivity is about 1.45 to about 1.55 millisiemens, and the protein content is at least about 95% by weight RTA as determined by SDS-PAGE.

19. Ricin toxin A chain of claim 12 including (f) chromatographing the eluted RTA using a phenylsepharose column, whereby the purity of the RTA is increased to above about 99%.

20. Ricin toxin A chain of claim 12 wherein steps a–f are singly or in combination run at a temperature that reduces formation of precipitates comprising RTA.

21. The method of claim 20 wherein said temperature is in a range from one sufficient to keep solutions from freezing to about 10° C.

22. The method of claim 20 wherein said temperature is about 4° C.

* * * * *